United States Patent
VanderStek et al.

(10) Patent No.: US 9,757,148 B2
(45) Date of Patent: Sep. 12, 2017

(54) SHORT-BEVEL NON-CORING NEEDLE

(71) Applicant: C. R. Bard, Inc., Murray Hill, NJ (US)

(72) Inventors: Bradley J. VanderStek, West Bountiful, UT (US); Daniel K. Smith, Woods Cross, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 237 days.

(21) Appl. No.: 14/213,467

(22) Filed: Mar. 14, 2014

(65) Prior Publication Data

US 2014/0276472 A1    Sep. 18, 2014

Related U.S. Application Data

(60) Provisional application No. 61/798,676, filed on Mar. 15, 2013.

(51) Int. Cl.
| | |
|---|---|
| *A61B 17/34* | (2006.01) |
| *A61M 5/32* | (2006.01) |
| *A61M 5/142* | (2006.01) |
| *A61M 25/00* | (2006.01) |

(52) U.S. Cl.
CPC ..... *A61B 17/3421* (2013.01); *A61M 5/14276* (2013.01); *A61M 5/329* (2013.01); *A61M 5/3286* (2013.01); *A61M 25/001* (2013.01)

(58) Field of Classification Search
CPC .......... A61M 5/3286; A61M 2005/341; A61M 2205/195; A61M 3/0279; A61M 25/001; A61M 25/0067; A61M 25/007; A61M 25/0084; A61M 2025/0091; A61M 5/329
See application file for complete search history.

(56) References Cited

U.S. PATENT DOCUMENTS

| | | | |
|---|---|---|---|
| 3,071,135 A | | 1/1963 | Baldwin et al. |
| 4,383,530 A | * | 5/1983 | Bruno ........................... 604/274 |
| 4,490,139 A | * | 12/1984 | Huizenga et al. .............. 604/57 |

(Continued)

FOREIGN PATENT DOCUMENTS

| | | |
|---|---|---|
| WO | 2009089090 A2 | 7/2009 |
| WO | 2012116315 A1 | 8/2012 |
| WO | 2014144681 A1 | 9/2014 |

OTHER PUBLICATIONS

PCT/US14/29197 filed Mar. 14, 2014 International Search Report and Written Opinion dated Aug. 20, 2014.

*Primary Examiner* — Imani Hayman
*Assistant Examiner* — Nilay Shah
(74) *Attorney, Agent, or Firm* — Rutan & Tucker, LLP (57) ABSTRACT

A non-coring needle for use in accessing an implanted medical device is disclosed. The non-coring needle is configured so as to include a compact bevel face relative to standard non-coring needles. In one embodiment, the non-coring needle comprises a hollow cannula that defines a lumen and terminates at a sharpened distal tip. The cannula includes a proximal portion and a bent distal portion. The distal portion defines a bevel face extending proximally from the distal tip, and the bevel face includes the lumen distal opening. The bevel face defines an open angle of at least about one degree with respect to a longitudinal axis of the proximal portion of the cannula. The bevel face is also laterally offset from the proximal portion of the cannula by an offset distance of no more than about 0.010 inch. A portion of the bevel face is dulled to prevent access port septum coring.

11 Claims, 6 Drawing Sheets

(56) References Cited

U.S. PATENT DOCUMENTS

| | | | |
|---|---|---|---|
| 4,586,926 A * | 5/1986 | Osborne | A61M 5/158 604/272 |
| 4,627,843 A * | 12/1986 | Raines | A61M 5/158 604/192 |
| 4,808,170 A | 2/1989 | Thornton et al. | |
| 4,889,529 A * | 12/1989 | Haindl | 604/274 |
| 5,217,442 A * | 6/1993 | Davis | A61M 5/14276 604/191 |
| 5,290,267 A * | 3/1994 | Zimmermann | 604/272 |
| 5,433,703 A | 7/1995 | Utterberg et al. | |
| 5,515,871 A * | 5/1996 | Bittner et al. | 128/898 |
| 5,607,407 A * | 3/1997 | Tolkoff | A61M 25/005 604/523 |
| 5,968,022 A | 10/1999 | Saito | |
| 6,273,877 B1 * | 8/2001 | West et al. | 604/264 |
| 6,517,523 B1 * | 2/2003 | Kaneko et al. | 604/272 |
| 6,926,693 B2 | 8/2005 | Enns | |
| 2003/0120267 A1 | 6/2003 | Kaufman et al. | |
| 2005/0049553 A1 * | 3/2005 | Triplett et al. | 604/110 |
| 2006/0064062 A1 | 3/2006 | Gurusamy et al. | |
| 2007/0179455 A1 | 8/2007 | Geliebter et al. | |
| 2007/0249939 A1 | 10/2007 | Gerbi et al. | |
| 2009/0131908 A1 | 5/2009 | McKay | |
| 2010/0181349 A1 * | 7/2010 | Carvalho | 222/566 |
| 2011/0208157 A1 | 8/2011 | Geliebter et al. | |
| 2012/0232499 A1 | 9/2012 | Stout et al. | |
| 2014/0242259 A1 * | 8/2014 | Young | 427/2.28 |

\* cited by examiner

SHORT-BEVEL NON-CORING NEEDLE

CROSS-REFERENCE TO RELATED APPLICATIONS

This application claims the benefit of U.S. Provisional Patent Application No. 61/798,676, filed Mar. 15, 2013, and titled "Short-Bevel Non-Coring Needle," which is incorporated herein by reference in its entirety.

BRIEF SUMMARY

Briefly summarized, embodiments of the present invention are directed to a non-coring Huber-type needle for use in accessing an implanted medical device. The non-coring needle is configured so as to include a compact bevel face relative to standard non-coring needles.

In one embodiment, the non-coring needle comprises a hollow cannula that defines a lumen and terminates at a sharpened distal tip. The cannula includes a proximal portion and a bent distal portion. The distal portion defines a bevel face extending proximally from the distal tip, and the bevel face includes the lumen distal opening. The bevel face defines an open angle of at least about one degree with respect to a longitudinal axis of the proximal portion of the cannula. The bevel face is also laterally offset from the proximal portion of the cannula by an offset distance of no more than about 0.010 inch. A portion of the bevel face is dulled to prevent access port septum coring. In addition, the compact bevel face reduces the insertion profile of the needle, which improves patient comfort.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle, while the needle end remaining outside the body is a proximal end of the needle. Also, the words "including," "has," and "having," as used herein, including the claims, shall have the same meaning as the word "comprising."

Embodiments of the present invention are generally directed to a non-coring needle for use in accessing an internal portion of a patient's body, such as to access an access port subcutaneously implanted within the patient, for instance, in order to deliver medicaments or other fluids to the patient, or to withdraw fluids therefrom. In accordance with one embodiment, the non-coring needle is configured so as to include a relatively compact distal portion. Indeed, in one embodiment, the bevel face of the distal portion of the needle is minimized in longitudinal length and insertion profile as compared to standard non-coring needles. This in turn enables the present needle to be larger in gauge relative to standard needles having comparably sized bevel faces, which correspondingly facilitates enhanced fluid flow through the needle.

Also, the shorter bevel face of the present needle assists in ensuring the entire bevel face of the needle resides within the reservoir of an access port when the needle is inserted into the port. Note that the principles discussed herein can be applied to needles of a variety of gauges and configurations, for use in various devices and with various applications. Note that, as used herein, a "Huber" or "Huber-type" needle is understood to include a non-coring needle that includes a beveled face at its distal end. The beveled face of the needle may include one or more facets thereon.

Figure 1:
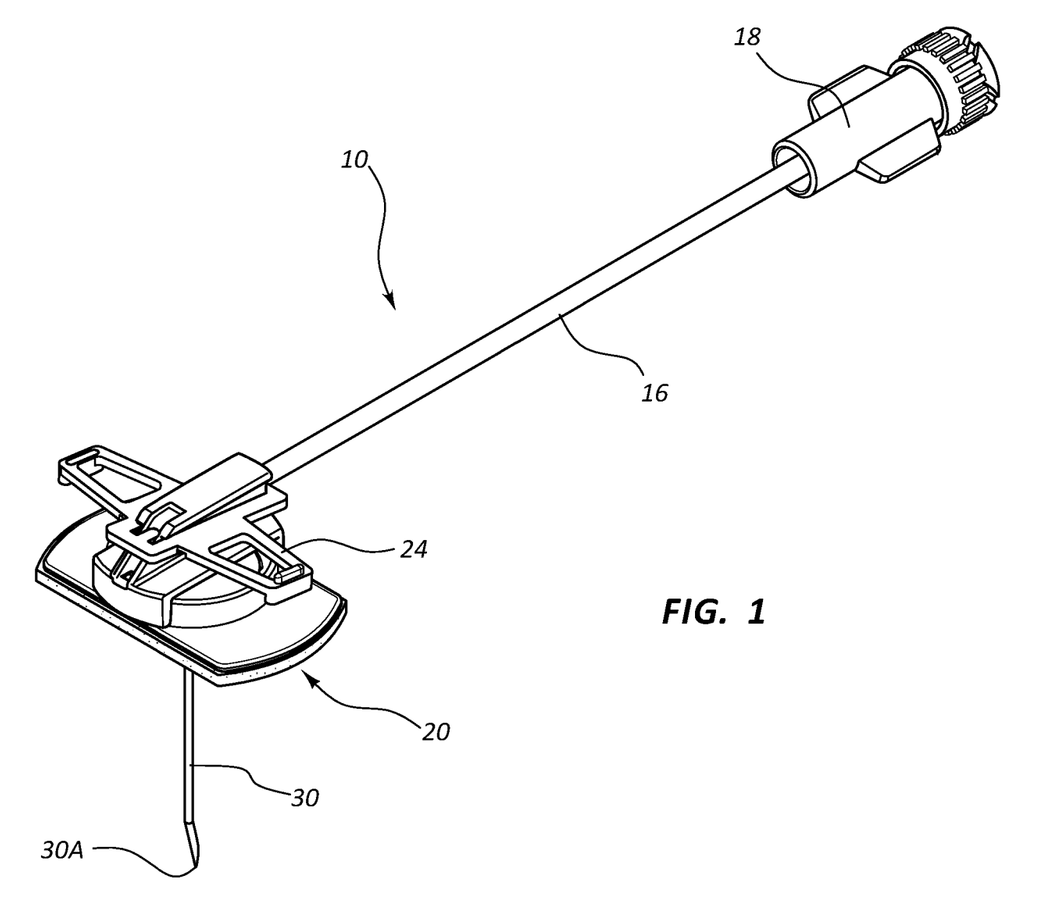
FIG. 1 is a perspective view of an infusion set according to one embodiment.

Reference is first made to FIG. 1, which describes details of a needle-based infusion set, generally designated at 10, as one example implementation where embodiments of the present disclosure can be practiced. As shown, the infusion set 10 includes a needle assembly 20, which in turn includes a needle hub 24 and a hollow needle 30 extending therefrom. The infusion set 10 further includes an extension leg 16 that defines a lumen that is in fluid communication with the needle 30 via the needle hub 24. A connector, such as a luer connector 18, is included on a proximal end of the extension leg 16 to enable the infusion set 10 to be operably connected to a fluid source, such as a syringe, vial, etc., or to a fluid repository in the case of fluid aspiration from the port through the infusion set.

The hollow needle 30 includes a distal tip 30A, which is inserted through the skin of a patient in order to access an internal body portion or implanted device. In one embodiment, the implanted device includes a subcutaneously disposed access port that is configured to establish fluid communication with the vasculature of the patient. When the distal tip 30A and distal portion of the infusion set needle 30 is operably inserted into the port, fluids can be infused into and/or aspirated from the port via the infusion set 10 and needle. Of course, other uses for the needle and other medical devices to be accessed can be contemplated. In one embodiment, for example, the needle 30 can be employed to assist in placing a catheter, such as an insulin infusion catheter, into the body of a patient.

Figure 2A:
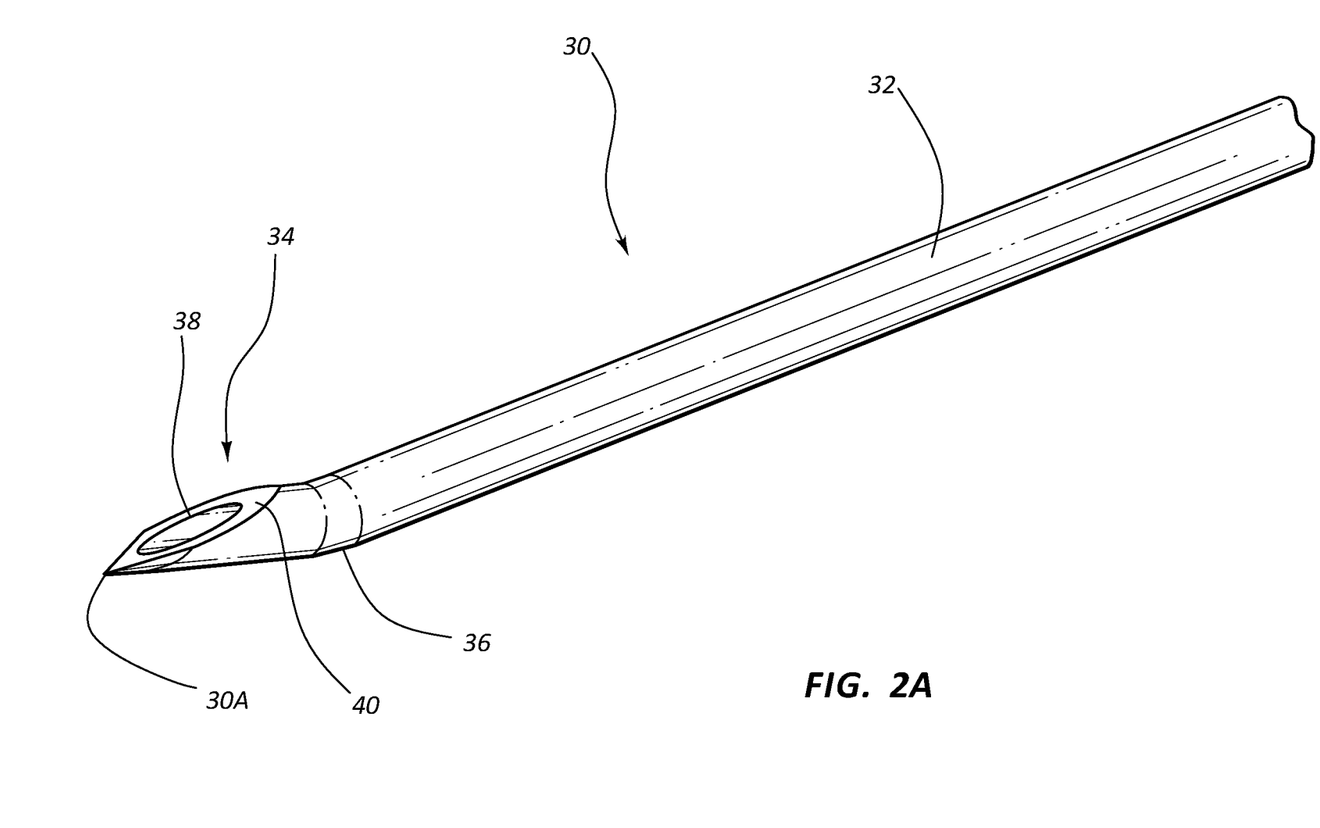
FIGS. 2A-2E are various views of a distal portion of a needle according to one embodiment.
Figure 2B:
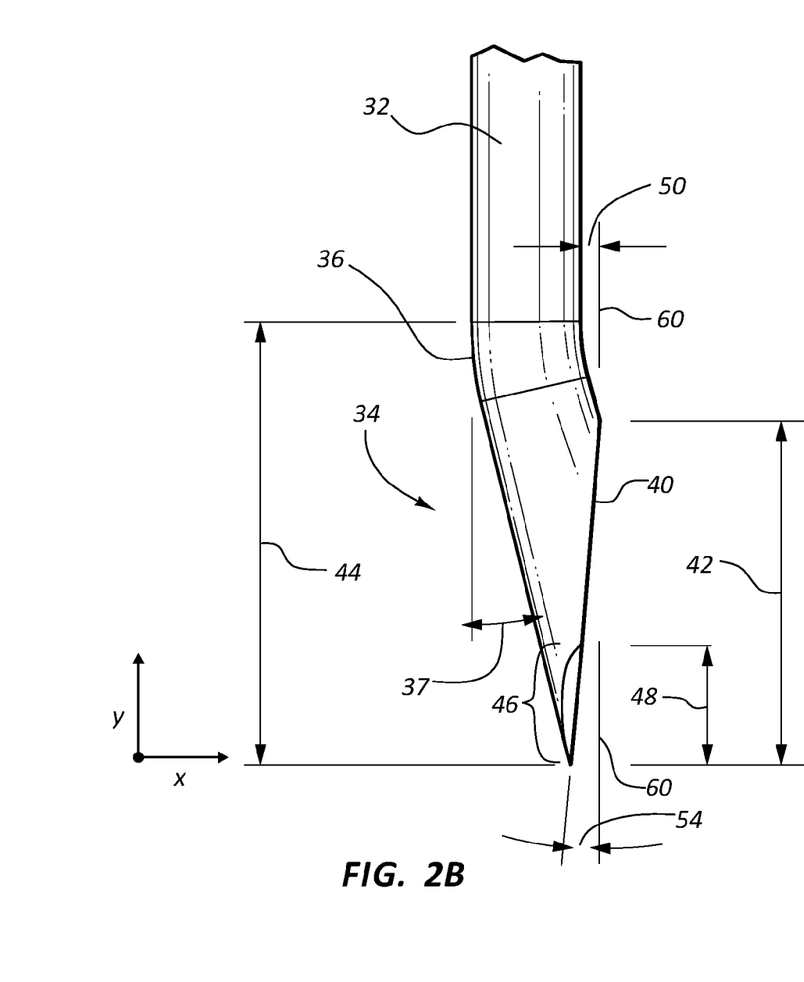
Figure 2C:
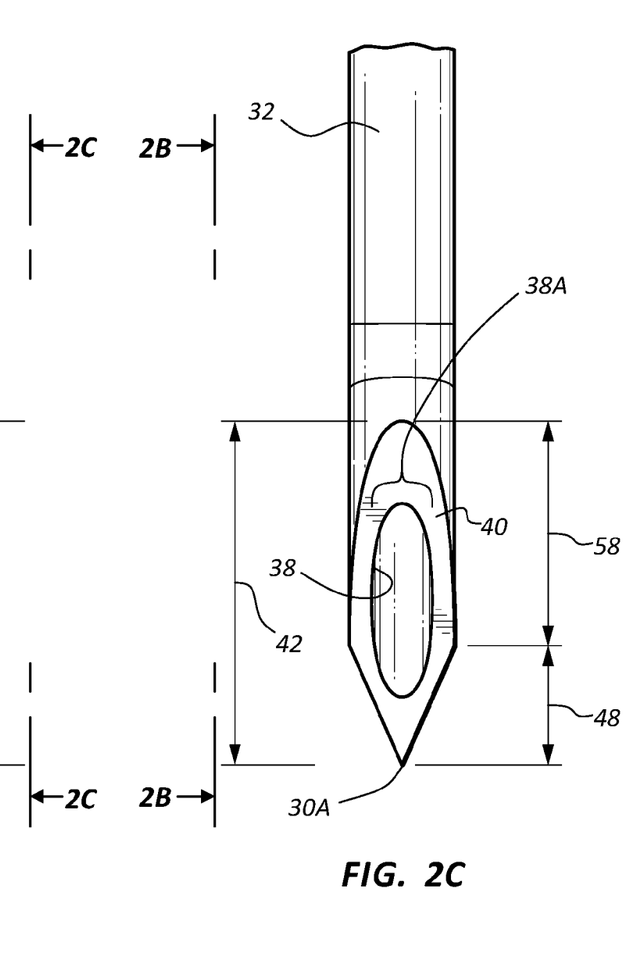
Figure 2D:
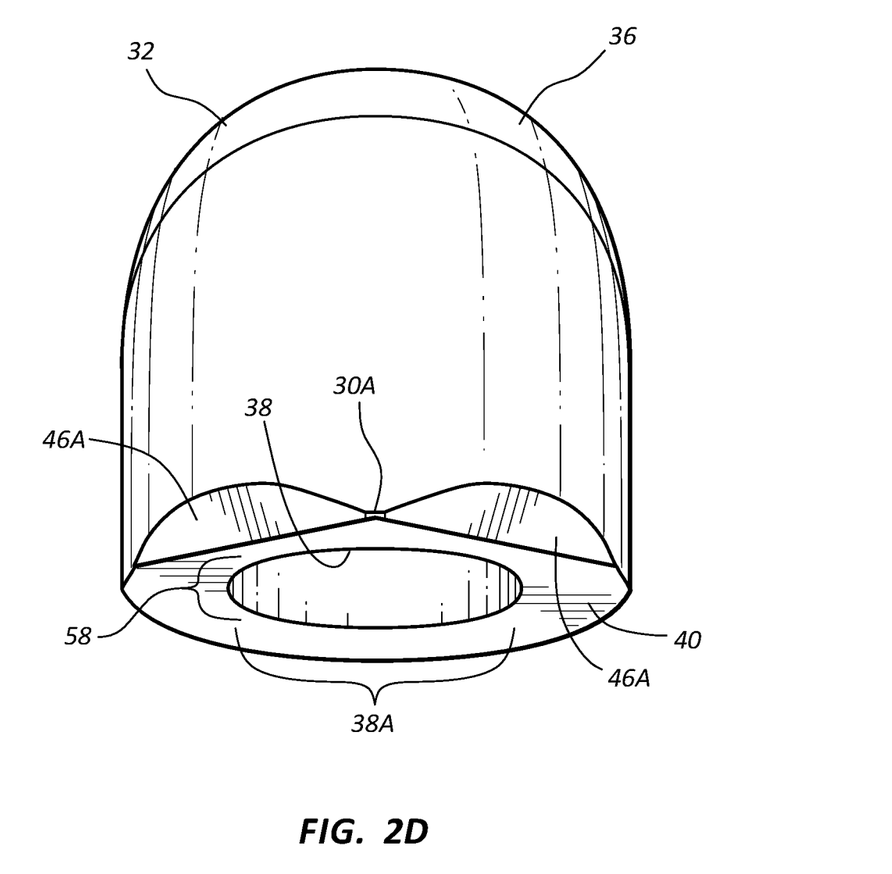
Figure 2E:
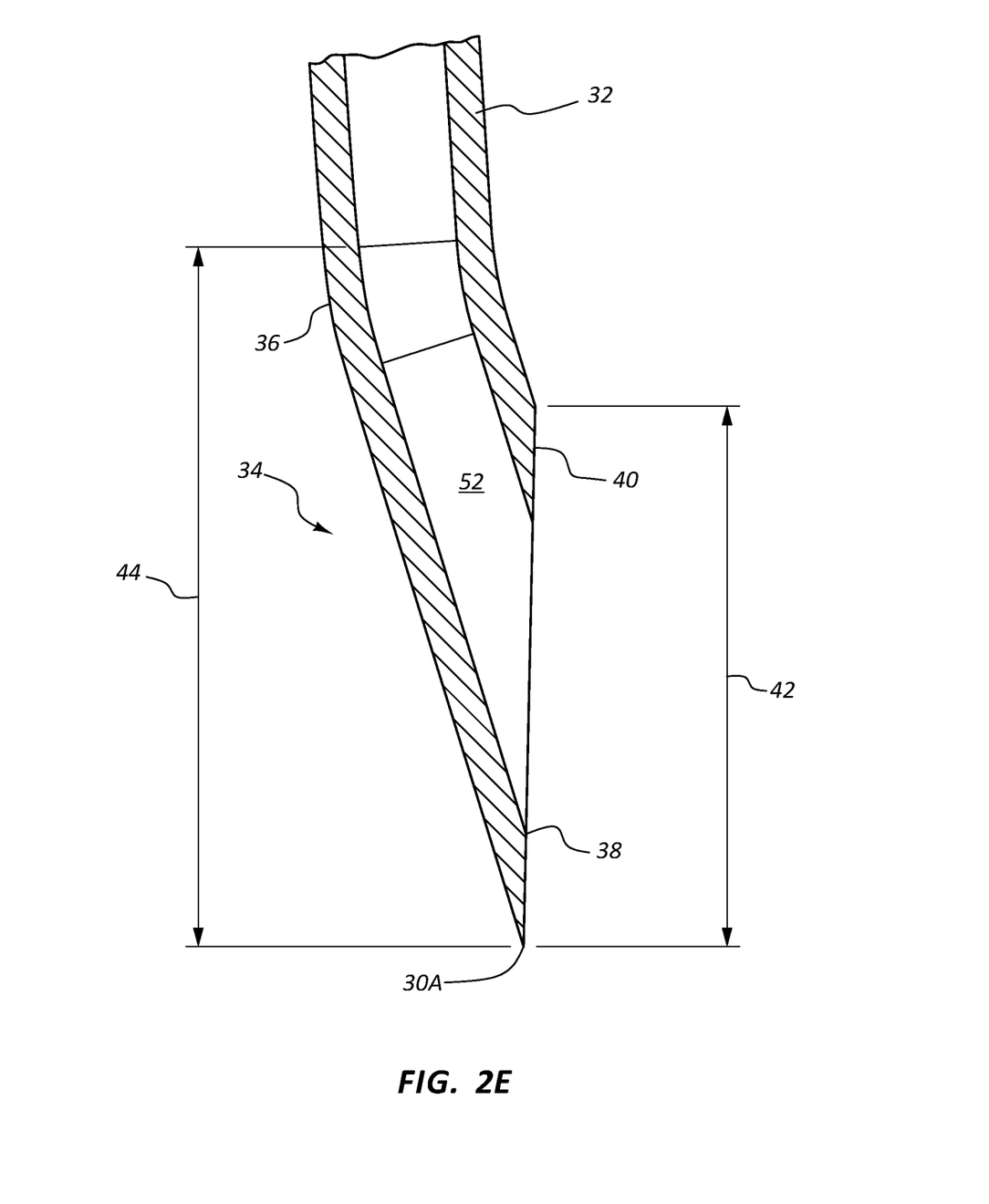

Reference is now made to FIGS. 2A-2E in describing further details regarding the needle 30 in accordance with one embodiment. As shown, the needle 30 includes a hollow shaft, or cannula 32. A proximal portion of the cannula 32 is substantially longitudinally straight, while a distal portion 34 having a bend length 44 (being measured along a y-axis of an x-y coordinate axis as shown in FIG. 2B) is bent with respect to the proximal portion at a bend 36. This results in the distal portion 34 being disposed at a bend angle 37 with respect to the proximal portion of the cannula 32. The bent configuration of the cannula distal portion 34 provides non-coring performance to the needle 30, similar to Huber-type needles. In one embodiment, the magnitude of the bend angle 37 is about 13 degrees, though other angles are possible. For example, in one non-limiting embodiment, the bend angle of the distal portion can vary from about 9 degrees to about 17 degrees. The distal portion 34 of the needle cannula 32 terminates at a sharpened distal tip 30A of the needle 30.

A terminal end of the needle cannula distal portion 34 defines a bevel face 40 that extends proximally from the needle distal tip 30A to define a bevel face length 42, the bevel face length being measured along the y-axis of an x-y coordinate axis as shown in FIG. 2B. A distal opening 38 of a lumen 52 (FIG. 2E) defined by the hollow cannula 32 is disposed on the bevel face 40. A chisel portion 46, including chisel faces 46A, is disposed adjacent the needle distal tip 30A to ease insertion of the needle 30 into the skin of the patient. The chisel portion 46 includes a chisel length 48, as measured along a y-axis of the x-y coordinate axis as shown in FIG. 2B.

As best seen in FIG. 2B, the bevel face 40 is angled to define an open bevel face angle 54, from a perspective at the distal end of the needle 30 looking proximally toward the needle hub 24 (FIG. 1). Though it can vary according to needle size or gauge, in the illustrated embodiment the magnitude of the bevel face angle 54 can be in the range of about one degree to about nine degrees, measured with respect to a line parallel to the longitudinal axis of the proximal portion of the cannula 32, such as an offset line 60 shown in FIG. 2B and discussed below. Again, other angles are possible. In the present embodiment, the bevel face angle 54 is about two degrees though, again, other angles are possible. The effect of the open-angle nature of the bevel face angle 54 can be seen in FIG. 2D, which shows the distal portion 34 of the needle 30 as viewed straight down the cannula 32. The open-angle nature of the bevel face 40 contrasts with traditional Huber-type needle tip designs, which include closed-angle configurations.

To eliminate the potential for partial coring of an access port septum during needle insertion (such coring otherwise potentially caused by the chisel faces 46A and the perimeter of the distal opening 38), a proximal portion 38A (FIGS. 2C, 2D), such as a proximal half, of the distal opening perimeter is dulled so as to prevent its ability to cut through a surface. In one embodiment, this is accomplished by bead blasting with glass or other suitable beads a dulling region 58 of the bevel face 40, which corresponds in the illustrated embodiment to approximately a proximal portion equaling about 75 percent of the bevel face length 42. Such a procedure is performed during manufacture of the needle 30. In addition, other dulling procedures may be performed on the dulling region different from or in addition to bead blasting, and regions larger or smaller than the dulling region indicated here may be treated.

As best seen in FIG. 2B, the bevel face 40 of the needle distal portion 34 is laterally offset from the cannula 32 in a positive direction along the x-axis of the x-y coordinate axis as shown in FIG. 2B. This lateral offset is indicated by an offset distance 50 in FIG. 2B, which is measured between the proximal end of the bevel face 40 (corresponding to offset line 60, which runs parallel to both the longitudinal axis of the proximal portion of the cannula 32 and the y-axis of the x-y coordinate axis shown in FIG. 2B) and the most proximate outer surface of the proximal portion of the cannula 32. The magnitude of the offset distance 50 is minimized as compared to traditional Huber-type needle designs, which include larger lateral offsets. Minimization of the offset distance 50 in the manner shown in FIG. 2B further reduces the longitudinal distance between the bend 36 and the top of the bevel face 40, as well as the bend length 44. In the illustrated embodiment, the magnitude of the offset distance is about 0.005 inch, though this value can vary according to needle design, gauge size, etc. In another embodiment, the magnitude of the offset distance is about 0.010 inch.

In accordance with one embodiment, the above-described configuration of the distal portion 34 of the needle cannula 32 enables the size and length 42 of the bevel face 40 to be smaller relative to the bevel faces of traditional Huber-type needles of the same gauge. In particular, minimization of the offset distance 50 in turn minimizes the length of the distal portion 34 of the needle distal to the bend 36. In addition, the open nature of the bevel face angle 54 provides a relatively larger distal opening 38 for the lumen of the cannula. These features of the needle 30 provide for a relatively large distal opening while maintaining a relatively small bevel face. Further, the minimization of the offset distance 50, together with the open bevel face angle 54 of the bevel face 40 discussed further above, desirably reduces the footprint, or profile, of the needle 30, as seen from the perspective shown in FIG. 2D. This in turn desirably reduces the perceived size of the needle 30.

Figure 3:
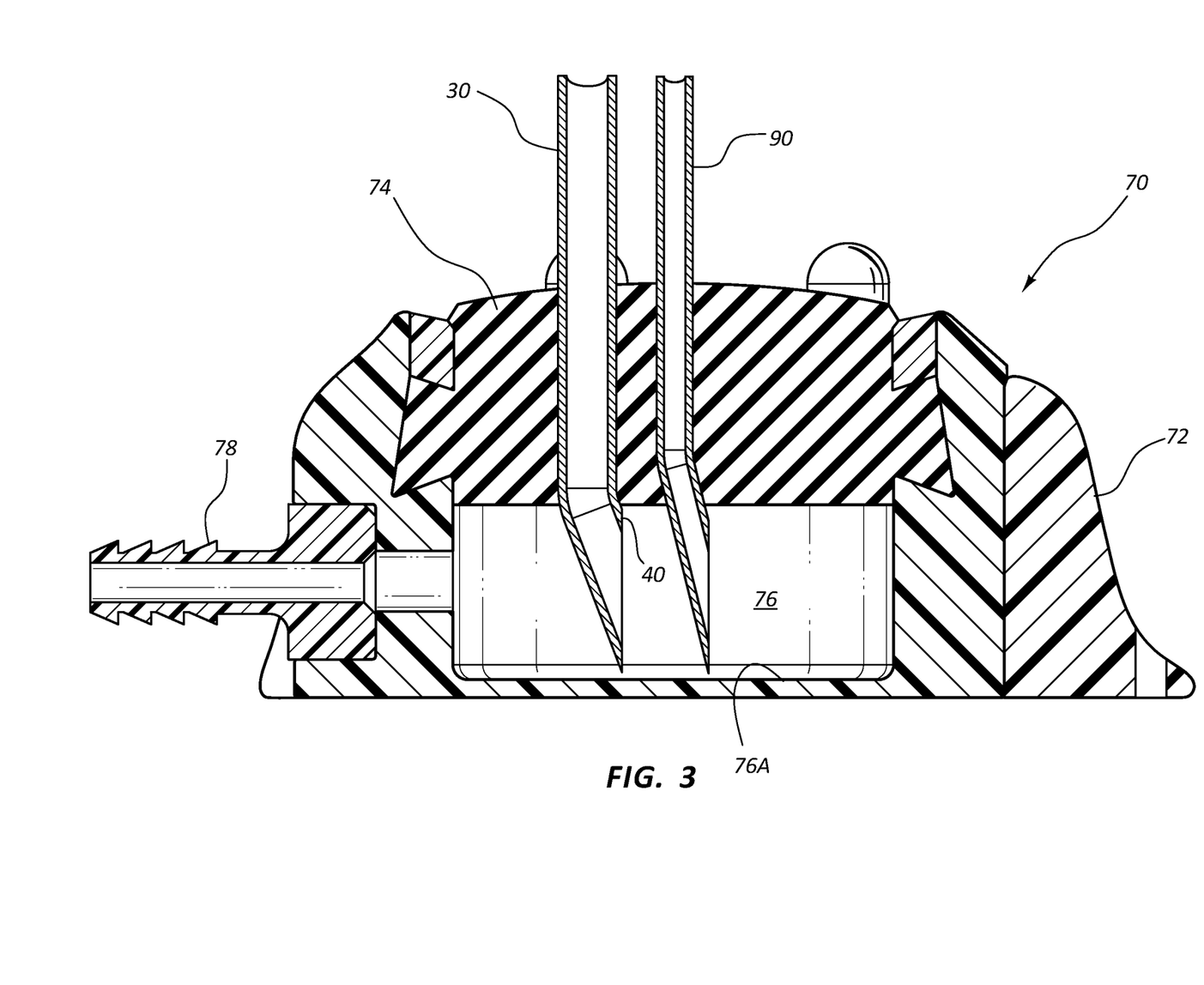
FIG. 3 is a cross-sectional view of an access port being accessed by needles, according to one embodiment.

The result of the above-described configuration of the needle distal portion 34 and bevel face 40 can be seen in FIG. 3, which depicts an access port 70 suitable for implantation into a body of a patient. As shown, the access port 70 includes a body 72 and a septum 74 that cooperate to define a fluid reservoir 76 with a bottom surface 76A. A stem 78 extends from the port 70 and is in fluid communication with the reservoir 76 to provide an outlet/inlet thereto.

The needle 30 described above in connection with FIGS. 2A-2E is shown inserted into the port 70 so as to pierce the septum 74 and seat in the reservoir 76 so that the entire bevel face 40 is disposed in the reservoir. A traditional Huber-type needle 90 is also shown similarly inserted into the port 70. The gauge size of the needle 30 is larger relative to the gauge size of the traditional needle 90. Nevertheless, the bevel faces of both needles are suitably disposed within the reservoir 76 so that fluid aspiration/infusion can occur without difficulty. This shows the ability of the present needle to desirably provide a relatively larger needle—with its corresponding relatively higher fluid flow rate—without a corresponding substantial increase in bevel face size. Correspondingly, the present needle 30 can be sized so as to provide the same needle gauge as a traditional Huber-type needle but with a relatively smaller bevel face, which in turn enables the reservoir of the access port to be smaller than what would otherwise be possible, thus desirably reducing the overall height of the access port.

In one embodiment, a process for manufacturing the needle 30 includes first rolling and drawing a metal tube to form the cannula 32, which cannula is then cut to desired length. A distal segment of the cannula 32 is then bent with respect to the proximal portion thereof to form the distal portion 34. The bevel face 40 is then ground to impart to the bevel face the open bevel face angle 54. The chisel faces 46A of the chisel portion 46 are then defined by grinding. The dulling region 58 of the bevel face 40 is then bead blasting with glass beads or other suitable media to dull the proximal portion 38A (e.g., the proximal half) of the distal opening 38. Note that the above process steps can be performed in a different order than what is given, and additional/alternative steps can be included.

In one embodiment, the needle 30 includes a gauge size of 18, a bend angle 37 of about 13 degrees, a bevel face length 42 of about 0.186 inch, a bend length 44 of about 0.196 inch, a chisel length 48 of about 20 percent to about 30 percent of the bevel face length, a bevel face angle 54 of about two degrees, and an offset distance 50 of about 0.005 inch.

In another embodiment, the needle 30 includes a gauge size of 22, a bend angle 37 of about 13 degrees, a bevel face length 42 of about 0.107 inch, a bend length 44 of about 0.119 inch, a chisel length 48 of about 20 percent to about 30 percent of the bevel face length, a bevel face angle 54 of about 2.5 degrees, and an offset distance 50 of about 0.005 inch.

In another embodiment, the needle 30 includes a gauge size of 23, a bend angle 37 of about 13 degrees, a bevel face length 42 of about 0.094 inch, a bend length 44 of about 0.108 inch, a chisel length 48 of about 20 percent to about 30 percent of the bevel face length, a bevel face angle 54 of about 2.5 degrees, and an offset distance 50 of about 0.005 inch.

In one embodiment, the needle 30 includes a gauge size of 25, a bend angle 37 of about 13 degrees, a bevel face length 42 of about 0.076 inch, a bend length 44 of about 0.093 inch, a chisel length 48 of about 20 percent to about 30 percent of the bevel face length, a bevel face angle 54 of about 2.5 degrees, and an offset distance 50 of about 0.005 inch. Note that the above dimensions for the different gauges of the needle 30 can vary and so should be understood as merely examples of the principles taught herein.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A non-coring needle, comprising:
   a cannula that terminates at a sharpened distal tip, the cannula defining a lumen that terminates at a distal opening, the cannula including a proximal portion and a distal portion, wherein:
   the distal portion of the cannula is disposed in a bent configuration with respect to the proximal portion of the cannula, the distal portion defining a bevel face extending proximally from the distal tip, a proximal portion of the bevel face extends laterally from a lateral edge of the proximal portion, a distal tip is laterally disposed between two axes, each axis being defined by opposing outer surfaces of the proximal portion, the bevel face including the distal opening of the lumen, the bevel face defining an open angle of at least about one degree with respect to a line parallel to a longitudinal axis of the proximal portion of the cannula; and
   at least a proximal half of a perimeter of the distal opening on the bevel face includes a dulled surface so as to prevent coring by the distal opening perimeter.

2. The needle as defined in claim 1, wherein the bevel face is laterally offset from the proximal portion of the cannula by an offset distance of no more than about 0.010 inch.

3. The needle as defined in claim 2, wherein the offset distance includes a magnitude of about 0.005 inch.

4. The needle as defined in claim 3, wherein the needle includes a gauge size of between 18 and 25.

5. The needle as defined in claim 1, wherein the needle includes a Huber-type needle.

6. The needle as defined in claim 1, wherein the needle is included as part of an infusion set and is suitable for infusion and aspiration of fluids therethrough.

7. The needle as defined in claim 1, wherein the needle is configured to access an implanted medical device within a body of a patient.

8. The needle as defined in claim 7, wherein the implanted medical device includes an access port.

9. The needle as defined in claim 1, wherein the open angle of the bevel face includes a magnitude of between about one degree and about nine degrees.

10. The needle as defined in claim 1, wherein the dulled surface includes 75% of a length of the bevel face.

11. The needle as defined in claim 1, wherein the sharpened distal tip terminates at a point.

* * * * *